(12) United States Patent
Lee et al.

(10) Patent No.: US 6,287,781 B1
(45) Date of Patent: Sep. 11, 2001

(54) METHOD FOR DETECTION OF TARGET NUCLEIC ACIDS USING PCR

(75) Inventors: Martin Alan Lee; Dario Lyall Leslie, both of Salisbury (GB)

(73) Assignee: The Secretary of State for Defence in Her Britannic Majesty's Government (GB)

( * ) Notice: Subject to any disclaimer, the term of this patent is extended or adjusted under 35 U.S.C. 154(b) by 0 days.

(21) Appl. No.: 09/622,426

(22) PCT Filed: Feb. 18, 1999

(86) PCT No.: PCT/GB99/00504

§ 371 Date: Oct. 19, 2000

§ 102(e) Date: Oct. 19, 2000

(87) PCT Pub. No.: WO99/42611

PCT Pub. Date: Aug. 26, 1999

(30) Foreign Application Priority Data

Feb. 19, 1998 (GB) .................................................. 9803382

(51) Int. Cl.[7] .............................. C12Q 1/68; C12P 19/34; C07H 21/04; C07H 21/00
(52) U.S. Cl. .............................. 435/6; 435/91.2; 435/800; 536/24.3; 536/25.32
(58) Field of Search ................................ 435/6, 91.2, 800; 536/24.3, 25.32

(56) References Cited

U.S. PATENT DOCUMENTS 5,567,583  10/1996  Wang et al. .............................. 435/6
5,866,336  * 2/1999  Nazarenko et al. ...................... 435/6
6,140,054  * 10/2000  Wittwer et al. .......................... 435/6

FOREIGN PATENT DOCUMENTS

WO96/34983  11/1996  (WO) .
WO97/29210   8/1997  (WO) .
WO97/46714  12/1997  (WO) .

* cited by examiner

Primary Examiner—Kenneth R. Horlick
Assistant Examiner—Alexander H. Spiegler
(74) Attorney, Agent, or Firm—Dean W. Russell; Kristin D. Mallatt; Kilpatrick Stockton LLP

(57) ABSTRACT

A method for detecting the presence of a target nucleic acid sequence in a sample is provided. The method comprises subjecting the sample to an amplification reaction to obtain an amplification product where the target nucleic acid sequence is present using a set of nucleotides, at least one of which is fluorescently labelled. The amplification product is contacted with a probe under conditions in which the probe will hybridise to the target sequence. The probe comprises a reactive molecule which is capable of absorbing fluorescence energy from or donating fluorescent energy to the fluorescent labelled nucleotide. The fluorescence of the sample is monitored and related to the presence of the target nucleic acid sequence. The method can be used to quantitate the amount of target nucleic acid in the sample as well as to determine sequence characteristics. Kits for effecting the method are also provided.

21 Claims, 1 Drawing Sheet

METHOD FOR DETECTION OF TARGET NUCLEIC ACIDS USING PCR

BACKGROUND OF THE INVENTION

1. Field of the Invention

The present invention provides a method for detecting a target polynucleotide in a sample, for example by monitoring an amplification reaction, preferably in a quantitative manner, as well as to probes and kits for use in these methods. The method is also suitable for the detection of sequence characteristics such as polymorphisms or allelic variation and so may be used in diagnostic methods

2. Description of the Related Art

Known fluorescence polymerase chain reaction (PCR) monitoring techniques include both strand specific and generic DNA intercalator techniques that can be used on a few second-generation PCR thermal cycling devices.

Generic methods utilise DNA intercalating dyes that exhibit increased fluorescence when bound to double stranded DNA species. Fluorescence increase due to a rise in the bulk concentration of DNA during amplifications can be used to measure reaction progress and to determine the target molecule copy number. Furthermore, by monitoring fluorescence with a controlled change of temperature, DNA melting curves can be generated, for example, at the end of PCR thermal cycling.

Generic DNA methods monitor the rise in bulk concentration of nucleic acids without any time penalty. A single fluorescent reading can be taken at the same point in every reaction. End point melting curve analysis can be used to discriminate artefacts from amplicon, and to discriminate amplicons. Peaks of products can be seen at concentrations that cannot be visualised by agarose gel electrophoresis.

In order to obtain high resolution melting data, the melt experiment must be performed slowly on existing hardware taking up to five minutes. However, by continually monitoring fluorescence amplification, a 3D image of the hysteresis of melting and hybridisation can be produced. This 3D image is amplicon dependent and may provide enough information for product discrimination.

It has been found that DNA melting curve analysis in general is a powerful tool in optimising PCR thermal cycling. By determining the melting temperatures of the amplicons, it is possible to lower the denaturing temperatures in later PCR cycles to this temperature. Optimisation for amplification from first generation reaction products rather than the genomic DNA, reduces artefact formation occuring in later cycles. Melting temperatures of primer oliaonucleotides and their complements can be used to determine their annealing temperatures, reducing the need for empirical optimisation.

The generic intercalator methods however are only quasi-strand-specific and are therefore not very useful where strand specific detection is required.

Strand specific methods utilise additional nucleic acid reaction components to monitor the progress of amplification reactions. These methods may use fluorescence energy transfer (FET) as the basis of detection. One or more nucleic acid probes are labelled with fluorescent molecules, one of which is able to act as an energy donor and the other of which is an energy acceptor molecule. These are sometimes known as a reporter molecule and a quencher molecule respectively. The donor molecule is excited with a specific wavelength of light for which it will normally exhibit a fluorescence emission wavelength. The acceptor molecule is also excited at this wavelength such that it can accept the emission energy of the donor molecule by a variety of distance-dependent energy transfer mechanisms. A specific example of fluorescence energy transfer which can occur is Fluorescence Resonance Energy Transfer or "FRET". Generally the acceptor molecule accepts the emission energy of the donor molecule when they are in close proximity (e.g. on the same, or a neighbouring molecule). The basis of FET or FRET detection is to monitor the changes at donor and acceptor emission wavelengths.

There are two commonly used types of FET or FRET probes, those using hydrolysis of nucleic acid probes to separate donor from acceptor, and those using hybridisation to alter the spatial relationship of donor and acceptor molecules.

Hydrolysis probes are commercially available as TaqMan™ probes. These consist of DNA oligonucleotides which are labelled with donor and acceptor molecules. The probes are designed to bind to a specific region on one strand of a PCR product. Following annealing of the PCR primer to this strand, Taq enzyme extends the DNA with 5' to 3' polymerase activity. Taq enzyme also exhibites 5' to 3' exonuclease activity. TaqMan™ probes are protected at the 3' end by phosphorylation to prevent them from priming Tag extension. If the TaqMan™ probe is hybridised to the product strand than an extending Taq molecule may also hydrolyse the probe, liberating the donor from acceptor as the basis of detection. The signal in this instance is cumulative, the concentration of free donor and acceptor molecules increasing with each cycle of the amplification reaction.

The fact that signal generation is dependent upon the occurrence of probe hydrolysis reactions means that there is a time penalty associated with this method. Furthermore, the presence of the probe may interrupt the smooth operation of the PCR process.

In addition, it has been found that hydrolysis can become non-specific, particularly where large numbers of amplification cycles, for instance more than 50 cycles, are required. In these cases, non-specific hydrolysis of the probe will result in an unduly elevated signal.

This means that such techniques are not very compatible with rapid PCR methods which are becoming more prominent with the development of rapid hot air thermal cyclers such as the RapidCycler™ and LightCycler™ from Idaho Technologies Inc. Other rapid PCR devices are described for example in co-pending British Patent Application Nos. 9625442.0 and 9716052.7. The merits of rapid cycling over conventional thermal cycling have been reported elsewhere. Such techniques are particularly useful for example in detection systems for biological warfare where speed of result is important if loss of life or serious injury is to be avoided.

Furthermore, hydrolysis probes do not provide significant information with regard to hysteresis of melting since signal generation is, by and large, dependent upon hydrolysis of the probe rather than the melt temperature of the amplicon.

Hybridisation probes are available in a number of guises. Molecular beacons are oligonucleotides that have complementary 5' and 3' sequences such that they form hairpin loops. Terminal fluorescent labels are in close proximity for FRET to occur when the hairpin structure is formed. Following hybridisation of molecular beacons to a complementary sequence the fluorescent labels are separated, so FRET does not occur, and this forms the basis of detection.

Pairs of labelled oligonucleotides may also be used. These hybridise in close proximity on a PCR product strand bringing donor and acceptor molecules together so that FRET can occur. Enhanced FRET is the basis of detection. Variants of this type include using a labelled amplification primer with a single adjacent probe.

The use of two probes, or a molecular beacon type of probe which includes two labelling molecules increases the cost involved in the process. In addition, this method requires the presence of a reasonably long known sequence so that two probes which are long enough to bind specifically in close proximity to each other are known. This can be a problem in some diagnostic applications, where the length of conserved sequences in an organism which can be used to design an effective probe, such as the HIV virus, may be relatively short.

Furthermore, the use of pairs of probes involves more complex experimental design. For example, a signal provided when by the melt of a probe is a function of the melting off of both probes. The study of small mismatches or where one of the probes is required to bind across a splice region (for example to detect RNA as compared to DNA in a sample where the sequence on either side of an intron can be utilised as the probe site) can yield incorrect results if the other probe melts first.

SUMMARY OF THE INVENTION

The applicants have developed an assay for detecting the presence of particular nucleic acid sequences which may be adapted to quantify the amount of the target sequence in the sample.

Thus the invention provides a method for detecting the presence of a target nucleic acid sequence in a sample, said method comprising (a) subjecting said sample to an amplification reaction using a set of nucleotides, at least one of which is fluorescently labelled, (b) contacting amplification product with a probe under conditions in which the probe will hybridise to said target sequence, said probe comprising a reactive molecule which is able to absorb fluorescence from or donate fluorescent energy to said fluorescent labelled nucleotide and (c)monitoring fluorescence of said sample.

DETAILED DESCRIPTION OF THE INVENTION

Figure 1:
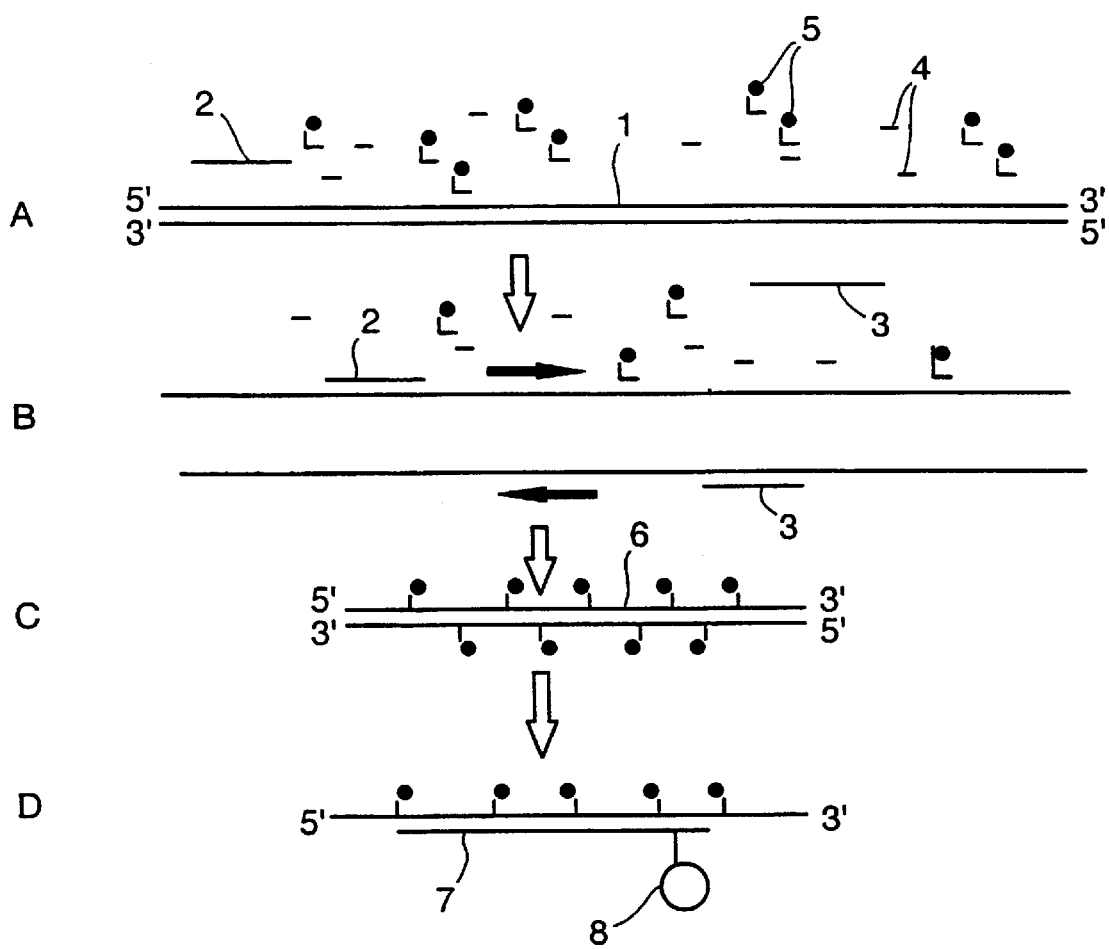
FIG. 1 shows diagrammatically the interactions which take place in the method of the invention.

Using an assay of this type, a fluorescent label becomes incorporated only into amplification product. When the probe hybridises to any specific target sequence produced as a result of the amplification reaction, the reactive molecule absorbs emission energy from labelled nucleotides or donates energy to the labelled nucleotides by means of FET or FRET, thus changing the signal from the fluorescent nucleotides. Suitably, the reactive molecule is able to absorb fluorescence from the labelled nucleotides and so the fluorescence from these is reduced. This reduction may be detected and this indicates binding of the probe.

Most preferably, the reactive molecule is an acceptor molecule which it emits fluorescence at a characteristic wavelength. In this case, increase in fluorescence from the acceptor molecule, which is of a different wavelength to that of the labelled nucleotide, will also indicate binding of the probe.

The presence of the thus labelled amplification product can be detected by monitoring fluorescence from the acceptor molecule on the probe, which specifically binds only the target sequence. In this case, signal from the amplification product can be distinguished from background signal of the fluorescent label and also from any non-specific amplification product.

The fact that the signal is partly associated with the amplification product and partly associated with the probe means that the system is highly specific in terms of detecting specific target sequences in reaction mixtures that contain large amounts of background DNA. This is because signal from non-specific amplification product can effectively be eliminated from the measured signal.

An assay of this nature can be carried out using inexpensive reagents. Single labelled probes are more economical to those which include both acceptor and donor molecules.

As used herein, the expression "set of nucleotides" refers to a group of nucleotides which are sufficient to form nucleic acids such as DNA and RNA. Thus these comprise adenosine, cytosine, guanine and thymine or uracil. One or more of these is fluorescently labelled. Labelled uracil is available from Boehringer Mannheim. Suitable fluorescent labels include fluorescein.

The use of labelled uracil may be particularly preferred in that its use may be built into the a strategy for preventing contamination or carry-over from one amplification reaction to subsequent ones carried out in the reaction vessels. Enzymes which digest uracil containing nucleic acids, such as uracil-N-glycosylase, can be used in a pre-cycling incubation step, to ensure that any residual amplicons are digested before thermal cycling in the subsequent application begins.

Suitably more than one nucleotide, and most preferably all the nucleotides are labelled as this will moderate the level of signal from the amplification product and thus the FET or FRET signal.

Amplification is suitably effected using known amplification reactions such as the polymerase chain reaction (PCR) or the ligase chain reaction (LCR), strand displacement assay (SDA) or NASBA, but preferably PCR.

Preferably, the fluorescence of both the nucleotide and the acceptor molecule are monitored and the relationship between the emissions calculated.

Suitable reactive molecules (such as acceptor molecules) are rhodamine dyes or other dyes such as Cy5. These may be attached to the probe in a conventional manner. The position of the reactive molecule along the probe is immaterial although it general, they will be positioned at an end region of the probe.

In order for FET, such as FRET, to occur between the reactive molecule and fluorescent emission of the nucleotides, the fluorescent emission of the element (reactive molecule or labelled nucleotide) which acts as the donor must be of a shorter wavelength than the element acceptor.

Suitable combinations are therefore set out in the following Table:

| Donor | Acceptor |
| --- | --- |
| SYBRGold | rhodamine |
| SYBRGreen I | rhodamine |
| SYBRGold | Cy5 |
| SYBRGreen I | Cy5 |
| Fluorescein | Ethidium bromide |

Preferably, the molecules used as donor and/or acceptor produce sharp peaks, and there is little or no overlap in the wavelengths of the emission. Under these circumstances, it may not be necessary to resolve the "strand specific peak"

from the signal produced by amplification product. A simple measurement of the strand specific signal alone (i.e. that provided by the reactive molecule) will provide information regarding the extent of the FET or FRET caused by the target reaction. The ethidium bromide/fluorescein combination may fulfill this requirement. In that case, the strand specific reaction will be quantifiable by the reduction in fluorescence at 520 nm, suitably expressed as 1/Fluorescence.

However, where there is a spectral overlap in the fluorescent signals from the donor and acceptor molecules, this can be accounted for in the results, for example by determining empirically the relationship between the spectra and using this relationship to normalise the signals from the two signals.

The method of the invention is extremely versatile in its applications. The method can be used to generate both quantitative and qualitative data regarding the target nucleic acid sequence in the sample, as discussed in more detail hereinafter. In particular, not only does the invention provide for quantitative amplification, but also it can be used, additionally or alternatively, to obtain characterising data such as duplex destabilisation temperatures or melting points.

In the method of the invention, the sample may be subjected to conditions under which the probe hybridises to the samples during or after the amplification reaction has been completed. The process allows the detection to be effected in a homogenous manner, in that the amplification and monitoring can be carried out in a single container with all reagents added intially. No subsequent reagent addition steps are required. Neither is there any need to effect the method in the presence of solid supports (although this is an option as discussed further hereinafter).

For example, where the probe is present throughout the amplification reaction, the fluorescent signal may allow the progress of the amplification reaction to be monitored. This may provide a means for quantitating the amount of target sequence present in the sample.

During each cycle of the amplification reaction, amplicon strands containing the target sequence bind to probe and thereby generate an acceptor signal. As the amount of amplicon in the sample increases, so the acceptor signal will increase. By plotting the rate of increase over cycles, the start point of the increase can be determined.

The probe may comprise a nucleic acid molecule such as DNA or RNA, which will hybridise to the target nucleic acid sequence when the latter is in single stranded form. In this instance, step (b) will involve the use of conditions which render the target nucleic acid single stranded. Alternatively, the probe may comprise a molecule such as a peptide nucleic acid which specifically binds the target sequence in double stranded form.

In particular, the amplification reaction used will involve a step of subjecting the sample to conditions under which any of the target nucleic acid sequence present in the sample becomes single stranded, such as PCR or LCR.

It is possible then for the probe to hybridise during the course of the amplification reaction provided appropriate hybridisation conditions are encountered.

In a preferred embodiment, the probe may be designed such that these conditions are met during each cycle of the amplification reaction. Thus at some point during each cycle of the amplification reaction, the probe will hybridise to the target sequence, and generate a signal as a result of the FET or FRET. As the amplification proceeds, the probe will be separated or melted from the target sequence and so the signal generated by the reactive molecule will either reduce or increase depending upon whether it comprises the donor or acceptor molecule. For instance, where it is an acceptor, in each cycle of the amplification, a fluorescence peak from the reactive molecule is generated. The intensity of the peak will increase as the amplification proceeds because more target sequence becomes available for binding to the probe.

By monitoring the fluorescence of the reactive molecule from the sample during each cycle, the progress of the amplification reaction can be monitored in various ways. For example, the data provided by melting peaks can be analysed, for example by calculating the area under the melting peaks and this data plotted against the number of cycles.

Fluorescence is suitably monitored using a known fluorimeter. The signals from these, for instance in the form of photo-multiplier voltages, are sent to a data processor board and converted into a spectrum associated with each sample tube. Multiple tubes, for example 96 tubes, can be assessed at the same time. Data may be collected in this way at frequent intervals, for example once every 10 ms, throughout the reaction.

The spectra generated in this way can be resolved, for example, using "fits" of pre-selected fluorescent moieties such as dyes, to form peaks representative of each signalling moiety (i.e. nucleotide label and/or reactive molecule). The areas under the peaks can be determined which represents the intensity value for each signal, and if required, expressed as quotients of each other. The differential of signal intensities and/or ratios will allow changes in FET or FRET to be recorded through the reaction or at different reaction conditions, such as temperatures. The changes, as outlined above, are related to the binding phenomenon between the probe and the target sequence. The integral of the area under the differential peaks will allow intensity values for the FET or FRET effects to be calculated.

This data provides one means to quantitate the amount of target nucleic acid present in the sample.

The probe may either be free in solution or immobilised on a solid support, for example to the surface of a bead such as a magnetic bead, useful in separating products, or the surface of a detector device, such as the waveguide of a surface plasmon resonance detector. The selection will depend upon the nature of the particular assay being looked at and the particular detection means being employed.

The probe may be designed such that it is hydrolysed by the DNA polymerase used in the amplification reaction thereby releasing the acceptor molecule. This provides a cumulative signal, with the amount of free reactive molecule present in the system increasing with each cycle. However, it is not necessary in this assay for the probe to be consumed in this way as the signal does not depend upon the hydrolysis of the probe.

In order to achieve a fully reversible signal which is directly related to the amount of amplification product present at each stage of the reaction, and/or where speed of reaction is of the greatest importance, for example in rapid PCR, it is preferable that the probe is designed such that it is released intact from the target sequence and so may take part again in the reaction. This may be, for example, during the extension phase of the amplification reaction. However, since the signal is not dependent upon probe hydrolysis, the probe may be designed to hybridise and melt from the target sequence at any stage during the amplification cycle, including the annealing or melt phase of the reaction. Such probes will ensure that interference with the amplification reaction is minimised.

Where probes which bind during the extension phase are used, their release intact may be achieved by using a 5'-3' exonuclease lacking enzyme such as Stoffle fragment of Taq or Pwo. This may be useful when rapid PCR is required as hydrolysis steps are avoided.

When used in this way, it is important to ensure that the probe is not extended during the extension phase of the reaction. Therefore, the 3' end of the probe is blocked, suitably by phosphorylation.

The data generated in this way can be interpreted in various ways. In its simplest form, an increase in fluorescence of the acceptor molecule in the course of or at the end of the amplification reaction is indicative of an increase in the amount of the target sequence present, suggestive of the fact that the amplification reaction has proceeded and therefore the target sequence was in fact present in the sample. However, as outlined above, quantitation is also possible by monitoring the amplification reaction throughout. Finally, it is possible to obtain characterisation data and in particular melting point analysis, either as an end point measure or throughout, in order to obtain information about the sequence as will be discussed further below.

Thus, a preferred embodiment of the invention comprises a method for detecting nucleic acid amplification comprising: performing nucleic acid amplification on a target polynucleotide in the presence of (a) a nucleic acid polymerase (b)at least one primer capable of hybridising to said target polynucleotide, (c) a set of nucleotides, at least one of which is fluorescently labelled and (d)an oligonucleotide probe which is capable of binding to said target polynucleotide sequence and which contains a reactive molecule which is capable of absorbing fluorescence from or donating fluorescence to the said labelled nucleotide; and monitoring changes in fluorescence during the amplification reaction. Suitably, the reactive molecule is an acceptor molecule which can absorb energy from the labelled nucleotide.

The amplification is suitably carried out using a pair of primers which are designed such that only the target nucleotide sequence within a DNA strand is amplified as is well understood in the art. The nucleic acid polymerase is suitably a thermostable polymerase such as Taq polymerase.

Suitable conditions under which the amplification reaction can be carried out are well known in the art. The optimum condltions may be variable in each case depending upon the particular amplicon involved, the nature of the primers used and the enzymes employed. The optimum conditions may be determined in each case by the skilled person. Typical denaturation temperatures are of the order of 95° C., typical annealing temperatures are of the order of 55° C. and extension temperatures are of the order of 72° C.

In a particular embodiment of the invention the probe may be used to quantitate RNA transcripts, for example in expression experiments, that maybe used in drug discovery. In particular this embodiment is suitable for expression studies in tissues from eukaryotic organisms. DNA encoding proteins in eukaryotic cells may contain introns, non-coding regions of DNA sequence, and exons that encode for protein sequence. Non-coding intron sequences are removed from RNA sequences that are derived from the DNA sequences during cellular "splicing" processes. PCR primers are normally targeted at coding regions and when reverse transcriptase PCR is used on total nucleic acid extracts, products will result from both DNA dependent amplification and RNA dependent amplification. Thus PCR alone, when used for expression studies, will contain amplification resulting from genomic DNA and expressed RNA.

A probe that is designed to bind across introns, on adjacent terminal regions of coding exons, will have limited interaction because of the intron region. Spliced RNA has these regions removed and therefore the adjacent terminal regions of coding exons form one continous sequence allowing efficient binding of the probe.

Conversely, a probe may detect only an amplification product of genomic DNA if it is designed such that it binds an intron region. Signal generated from such a probe would relate only to the DNA concentration and not the RNA concentration of the sample.

Thus in a further embodiment, the probe is specific either for a splice region of RNA or an intron in DNA, so that only one of amplified RNA or amplified DNA is detected and/or quantitated.

Alternatively or additionally, the method of the invention can be used in hybridisation assays for determining characteristics of a sequence. Thus in a further aspect, the invention provides a method for determining a characteristic of a sequence, said method comprising (a) amplifying said sequence using a set of nucleotides, at least one of which is fluorescently labelled, (b) contacting amplification product with a probe under conditions in which the probe will hybridise to said target sequence, said probe comprising a reactive molecule which is able to absorb fluorescence from or donate fluorescent energy to said fluorescent labelled nucleotide and (c)Monitoring fluorescence of said sample and determining a particular reaction condition, characteristic of said sequence, at which fluorescence changes as a result of the hybridisation of the probe to the sample or destabilisation of the duplex formed between the probe and the target nucleic acid sequence.

Suitable reaction conditions include temperature, electrochemical, or the response to the presence of particular enzymes or chemicals. By monitoring changes in fluorescence as these properties are varied, information characteristic of the precise nature of the sequence can be achieved. For example, in the case of temperature, the temperature at which the probe separates from the sequences in the sample as a result of heating can be determined. This can be extremely useful in for example, to detect and if desired also to quantitate, polymorphisms and/or allelic variation in genetic diagnosis. By "polymorphism" is included transitions, transversions, insertions, deletions of inversions which may occur in sequences, particularly in nature.

The hysteresis of melting will be different if the target sequence varies by only one base pair. Thus for example, where a sample contains only a single allelic variant, the temperature of melting of the probe will be a particular value which will be different from that found in a sample which contains only another allelic variant. A sample containing both allelic variants which show two melting points corresponding to each of the allelic variants. Similar considerations apply with respect to electrochemical properties, or in the presence of certain enzymes or chemicals. The probe may be immobilised on a solid surface across which an electrochemical potential may be applied. Target sequence will bind to or be repulsed from the probe at particular electrochemical values depending upon the precise nature of the sequence.

In addition, the kinetics of probe hybridisation will allow the determination, in absolute terms, of the target sequence concentration. Changes in fluorescence from the sample can allow the rate of hybridisation of the probe to the sample to be calculated. An increase in the rate of hybridisation will relate to the amount of target sequence present in the sample. As the concentration of the target sequence increases as the amplification reaction proceeds, hybridisation of the probe will occur more rapidly. Thus this parameter also can be used as a basis for quantification. This mode of data processing useful in that it is not reliant on signal intensity to provide the information.

Further aspects of the invention include kits for use in the method of the invention. These kits will contain a probe specific for a target nucleotide sequence which contains a reactive molecule, in particular an acceptor molecule. If desired, the probe can be immobilised on a support such as a bead, for example a magnetic bead, or a support used in a detector, such as the waveguide of an evanescent wave detector device.

Additionally, kits may contain one or more fluorescently labelled nucleotides which is/are compatible with said reactive molecule. Other potential components of the kit include reagents used in amplification reactions such as DNA polymerase.

The invention will now be particularly described by way of example with reference to the accompanying diagrammatic drawings in FIG. 1:

In the illustrated amplification reaction, a DNA molecule (1) prepared for amplification by contacting it with pair of amplification primers (2), (3) and a set of nucleotides (4) some of which are labelled with a fluorescent label (5) (FIG 1A). The DNA molecule (1) is rendered single stranded (FIG. 1B) whereupon the primers (2,3) bind as forward and reverse primers in an amplification reaction as is well known.

During the course of the subsequent amplification reaction, an amplicon product (6) is built up (FIG. 1C). Nucleotides both labelled and unlabelled are incorporated into the product as it is formed. In the normal way, the amplicon product (6) contains only the target sequence as defined by the primers.

When this product is melted during the subsequent phase of the amplification, probe (7) comprising an acceptor molecule (8) binds the target sequence (FIG. 1D). The FRET interaction between the fluorescent nucleotides and the acceptor molecule (8) means generates a signal at the wavelength characteristic of the acceptor.

The acceptor signal (8) can then be monitored using conventional fluorescence detection devices.

What is claimed is:

1. A method for detecting the presence of atarget nucleic acid sequence in a sample, said method comprising (a) subjecting said sample to an amplification reaction to obtain an amplification product where the target nucleic acid sequence is present, using a set of nucleotides, at least one of which is fluorescently labeled, (b) contacting the amplification product with a probe under conditions in which the probe will hybridise to said target sequence, said probe comprising a reactive molecule which is capable of absorbing fluorescence energy from or donating fluorescent energy to said fluorescent labeled nucleotide and (c) monitoring fluorescence of said sample; and (d) relating the fluorescence of the sample to detect the presence of the target nucleic acid sequence.

2. A method according to claim 1, wherein in the reactive molecule absorbs fluorescence from said fluorescent labeled nucleotide.

3. A method according to claim 2, wherein the reactive molecule is an acceptor molecule which emits energy at a characteristic wavelength.

4. A method according to claim 3, wherein the acceptor molecule is a rhodamine dye or other dye such as Cy5.

5. A method according to claim 1, wherein the labeled nucleotide is labeled uracil.

6. A method according to claim 1, wherein all nucleotides used in the amplification reaction are labeled.

7. A method according to claim 1, wherein the amplification reaction comprises the polymerase chain reaction (PCR).

8. A method according to claim 1, further comprising: monitoring fluorescent emissions of both the labeled nucleotide and the reactive molecule; and calculating the relationship between the emissions.

9. A method according to claim 1, wherein the probe is present throughout the amplification reaction.

10. A method according to claim 9, wherein the fluorescence is monitored to obtain fluorescence results, wherein the results used to quantitate the amount of target sequence present in the sample.

11. A method according to claim 1, wherein the amplification reaction includes a DNA polymerase, wherein the probe is designed such that it is hydrolyzed by the DNA polymerase used in the amplification reaction.

12. A method according to claim 1, wherein the amplification reaction includes an extension phase, wherein the probe is designed such that during the extension phase of the amplification reaction, the probe is released intact from the target sequence.

13. A method according to claim 12, wherein the amplification reaction is effected using a 5'-3' exonuclease lacking enzyme.

14. A method according to claim 13, wherein the enzyme is Stoffle fragment of Taq or Pwo.

15. A method according to claim 12, wherein the 3' end of the probe is blocked by phosphorylation.

16. A method for detecting nucleic acid amplification comprising: performing nucleic acid amplification on a target polynucleotide in the presence of (a) a nucleic acid polymerase (b) at least one primer capable of hybridizing to said target polynucleotide, (c) a set of nucleotides, at least one of which is fluorescently labeled and (d) an oligonucleotide probe which is capable of binding to said target polynucleotide sequence and which contains a reactive molecule which is capable of absorbing fluorescence energy from or donating fluorescent energy to the said labeled nucleotide; and monitoring charges in fluorescence during the amplification reaction, wherein changes in the fluorescence are indicative of the nucleic acid amplification reaction.

17. A method according to claim 16, wherein the amplification is carried out using a pair of primers.

18. A method according to any one of 1 or 16, "claims" wherein the probe is specific either for a splice region of RNA or an intron in DNA, so that only one of amplified RNA or amplified DNA is detected and/or quantitated.

19. A method for determining a reaction condition at which a sequence hybridizes to or separates from a probe, said method comprising (a) amplifying said sequence using a set of nucleotides, at least one of which is fluorescently labeled, (b) contacting amplification product with a probe under condition in which the probe will hybridize to said target sequence, said probe comprising a reactive molecule which is capable of absorbing fluorescence energy from or donating fluorescent energy to said fluorescent labeled nucleotide and (c)monitoring fluorescence of said sample and determining a particular reaction condition, characteristic of said sequence, at which fluorescence changes as a result of the hybridization of the probe to the sample or destabilization of the duplex formed between the probe and the target nucleic acid sequence.

20. A method for detecting a polymorphisms and/or allelic variation, said method comprising amplifying a sequence suspected of containing said polymorphism or variation using the method as defined in claim 1, to obtain an amplification product, generating a flourescence signal measuring the temperature at which the probe melts from the amplification product using the fluorescent signal generated, and comparing this temperature to the temperature at which a sequence not having a polymorphism and/or allelic variation melts from said probe in order to detect the polymorphism and/or allelic variation.

21. A kit for use in the method of any one of claims 1, 16, 19, or 20, which comprises a fluorescently labeled nucleotide and a probe specific for a target nucleotide sequence, the probe comprising a reactive molecule which is capable of absorbing fluorescence from or donating fluorescent energy to said fluorescently labeled nucleotide.

* * * * *